(12) United States Patent
Ben-David et al.

(10) Patent No.: US 8,890,087 B2
(45) Date of Patent: Nov. 18, 2014

(54) WATER PURIFICATION APPARATUS COMPRISING AN UV SOURCE

(75) Inventors: Jonathan Ben-David, Basingstoke (GB); Heung Soon Kim, Qingdao (CN)

(73) Assignee: WLI Trading Limited, Dublin (IE)

( * ) Notice: Subject to any disclaimer, the term of this patent is extended or adjusted under 35 U.S.C. 154(b) by 0 days.

(21) Appl. No.: 13/503,909

(22) PCT Filed: Oct. 26, 2010

(86) PCT No.: PCT/GB2010/051795
§ 371 (c)(1),
(2), (4) Date: Jun. 12, 2012

(87) PCT Pub. No.: WO2011/051708
PCT Pub. Date: May 5, 2011

(65) Prior Publication Data
US 2012/0241644 A1  Sep. 27, 2012

(30) Foreign Application Priority Data

Oct. 27, 2009 (GB) .................................. 0918824.4
Mar. 8, 2010 (GB) .................................. 1003794.3

(51) Int. Cl.
*C02F 1/32* (2006.01)
*C02F 3/00* (2006.01)
*A61L 2/10* (2006.01)

(52) U.S. Cl.
CPC ......... *C02F 1/325* (2013.01); *C02F 2201/3223* (2013.01); *A61L 2/10* (2013.01); *C02F 2301/022* (2013.01); *C02F 2201/3228* (2013.01); *C02F 2301/026* (2013.01); *C02F 2201/3227* (2013.01)
USPC .......... 250/437; 422/186.3; 422/24; 250/435; 250/436; 250/438; 250/455.11; 210/748.1; 210/748.11

(58) Field of Classification Search
CPC ................................... C02F 1/325; A61L 2/10
USPC .................. 250/455.11, 435–438; 210/748.1; 422/24
See application file for complete search history.

(56) References Cited

U.S. PATENT DOCUMENTS 4,676,896 A * 6/1987 Norton .......................... 210/192
4,956,754 A   9/1990 Chen
(Continued)

FOREIGN PATENT DOCUMENTS

CN         201312923 Y     9/2009
DE   10 2007 055 449 A1   12/2008
(Continued)

OTHER PUBLICATIONS

International Search Report and Written Opinion for corresponding International Application No. PCT/GB2010/051795, mailed Jan. 20, 2011, 10pp.

(Continued)

*Primary Examiner* — Jack Berman
*Assistant Examiner* — James Choi
(74) *Attorney, Agent, or Firm* — Christie, Parker & Hale, LLP

(57) ABSTRACT

Water purification apparatus, comprising an elongate UV source and a conduit for water to be purified formed of a UV transmissive material, wherein the conduit has an inlet and an outlet and positioned so that part of it is wrapped around at least part of the UV source thereby to sterilize water within the conduit, further comprising reflective means for UV radiation to be reflected onto one or more parts of the conduit which extends beyond the part which is wrapped around the UV source.

25 Claims, 14 Drawing Sheets

(56) References Cited

U.S. PATENT DOCUMENTS

| | | | |
|---|---|---|---|
| 5,069,782 A | 12/1991 | Moyher, Jr. et al. | |
| 5,725,757 A | 3/1998 | Binot | |
| 5,942,110 A | 8/1999 | Norris | |
| 6,268,607 B1 * | 7/2001 | Marsh et al. | 250/455.11 |
| 6,946,651 B1 | 9/2005 | Bohne | |
| 7,030,391 B2 | 4/2006 | Zagrobelny | |
| 7,252,763 B2 | 8/2007 | Kuennen et al. | |
| 7,304,312 B2 | 12/2007 | Hopaluk et al. | |
| 7,416,588 B2 | 8/2008 | Burrows et al. | |
| 8,729,500 B2 * | 5/2014 | Mastenbroek et al. | 250/455.11 |
| 2003/0086831 A1 * | 5/2003 | Horton, III | 422/120 |
| 2005/0109690 A1 | 5/2005 | Bechtold | |
| 2005/0156119 A1 * | 7/2005 | Greene | 250/436 |
| 2007/0272877 A1 * | 11/2007 | Tribelsky et al. | 250/431 |
| 2007/0274879 A1 * | 11/2007 | Millikin | 422/186.3 |
| 2008/0224066 A1 | 9/2008 | Nolen et al. | |
| 2008/0305018 A1 * | 12/2008 | Blum | 422/186.3 |
| 2009/0285727 A1 | 11/2009 | Levy | |
| 2010/0002451 A1 * | 1/2010 | Reynolds | 362/363 |
| 2011/0174993 A1 * | 7/2011 | Blain | 250/492.1 |
| 2011/0210268 A1 * | 9/2011 | Dornseifer | 250/436 |
| 2012/0011874 A1 | 1/2012 | Conradt et al. | |

FOREIGN PATENT DOCUMENTS

| | | |
|---|---|---|
| EP | 1 440 941 B1 | 7/2004 |
| EP | 1 755 690 B1 | 2/2007 |
| JP | 59-115778 | 7/1984 |
| JP | 59-115778 A | 7/1984 |
| JP | 62-114694 A | 5/1987 |
| JP | EP 0277505 B1 * | 1/1988 |
| JP | 63-186286 U | 11/1988 |
| JP | 6-320153 | 11/1994 |
| JP | 8-66677 A | 3/1996 |
| JP | 9-276857 A | 10/1997 |
| JP | 2004-66045 | 3/2004 |
| JP | 2004-122008 | 4/2004 |
| JP | 2005-279649 A | 10/2005 |
| WO | WO 95/13853 A1 | 5/1995 |
| WO | WO 2005/102401 A2 | 11/2005 |
| WO | WO 2009/024155 A1 | 2/2009 |
| WO | WO 2010/004027 A1 | 1/2010 |
| WO | WO 2010/004028 A1 | 1/2010 |
| WO | WO 2010004027 A1 * | 1/2010 |

OTHER PUBLICATIONS

Search Report for corresponding Application No. GB0918824.4, dated Feb. 23, 2010, 1pg.

Search Report for corresponding Application No. GB1003794.3, dated Jul. 8, 2010, 2pp.

* cited by examiner

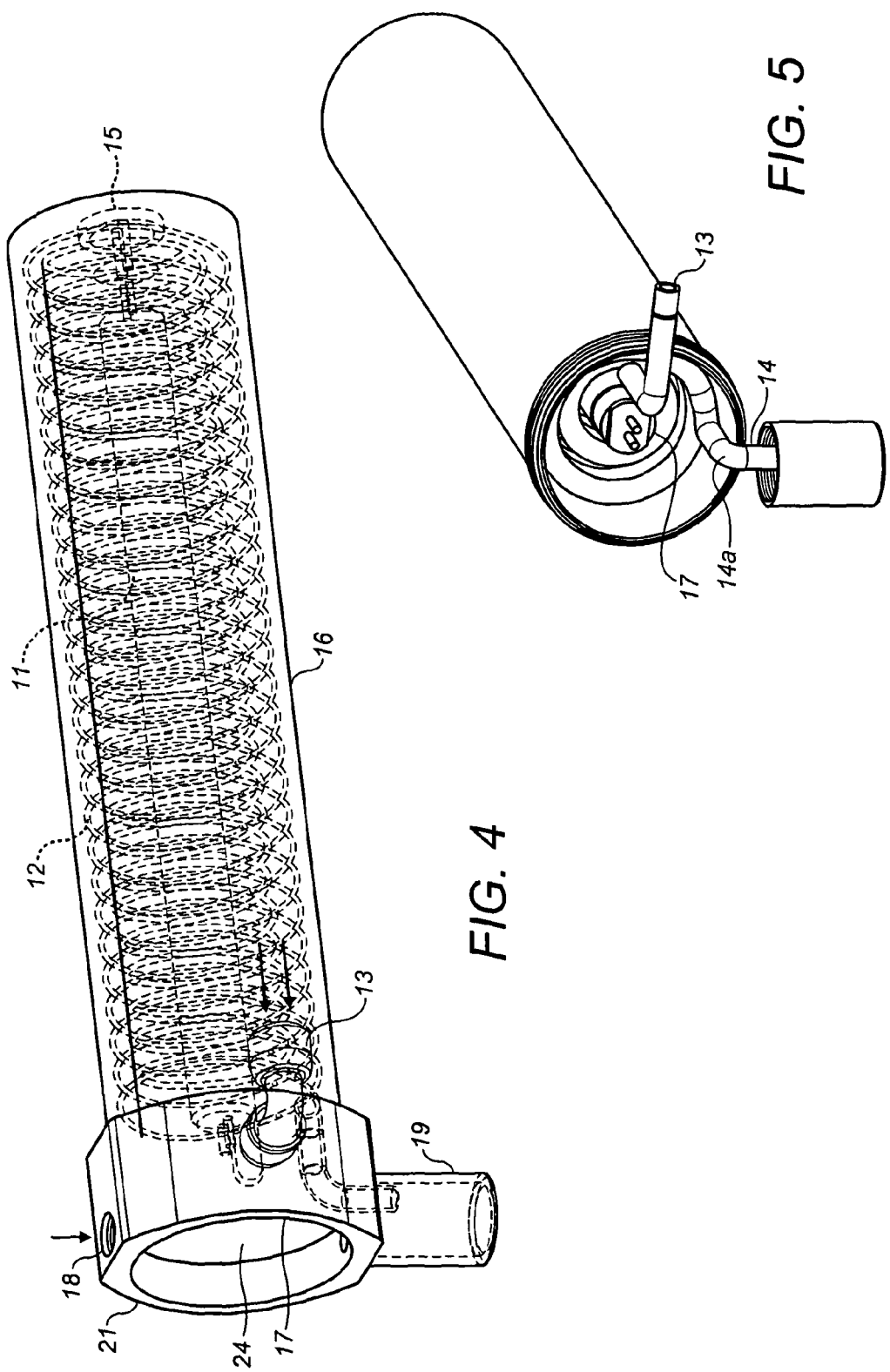

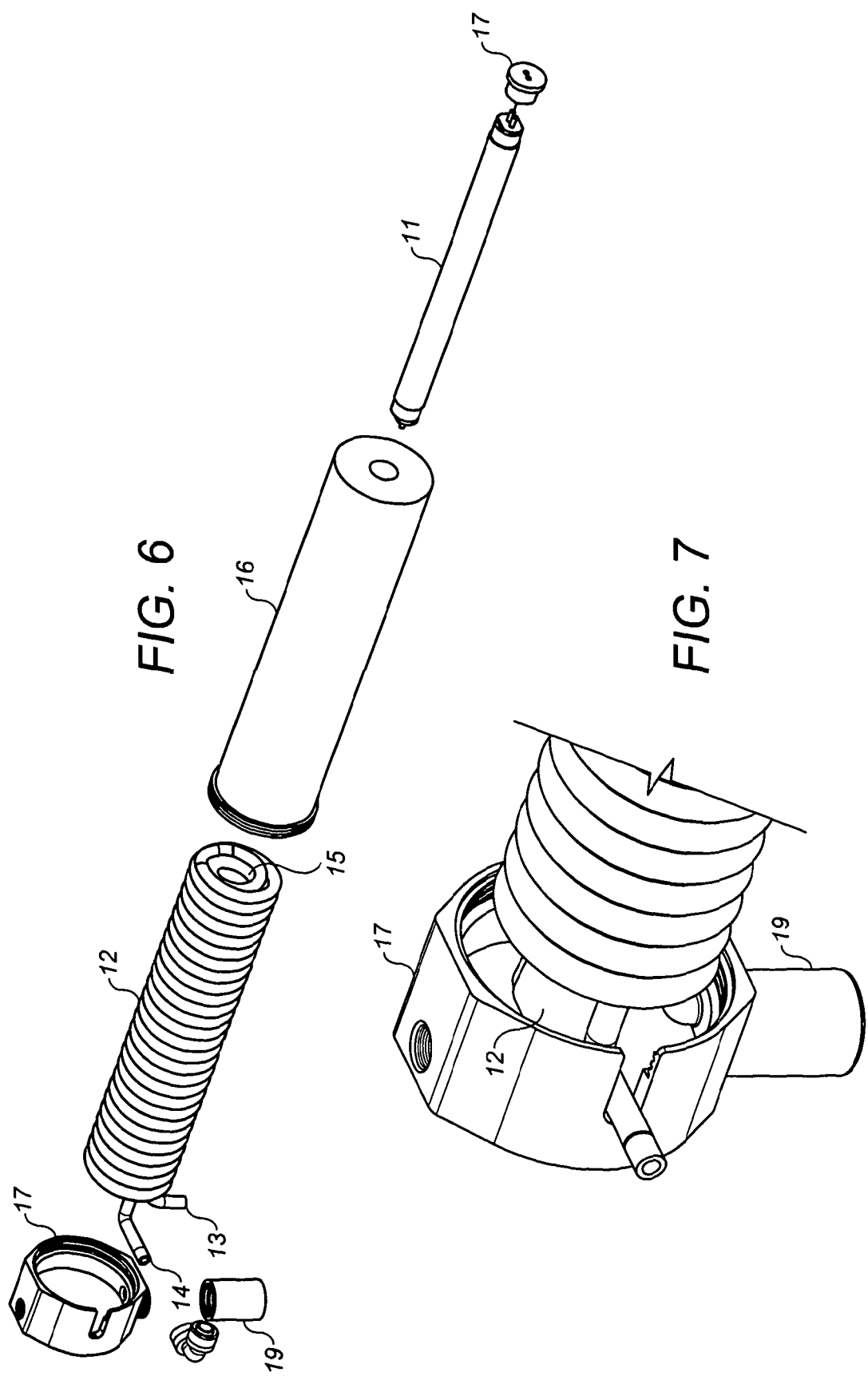

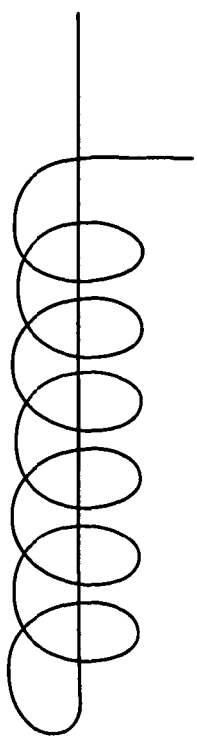
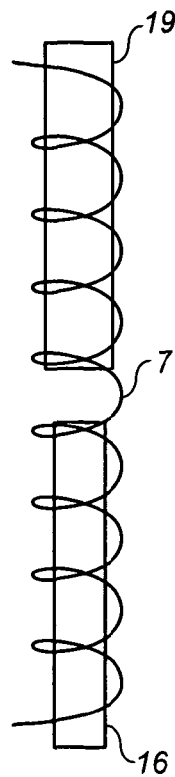
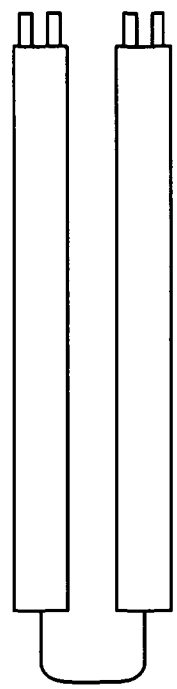
FIG. 21  FIG. 22  FIG. 23
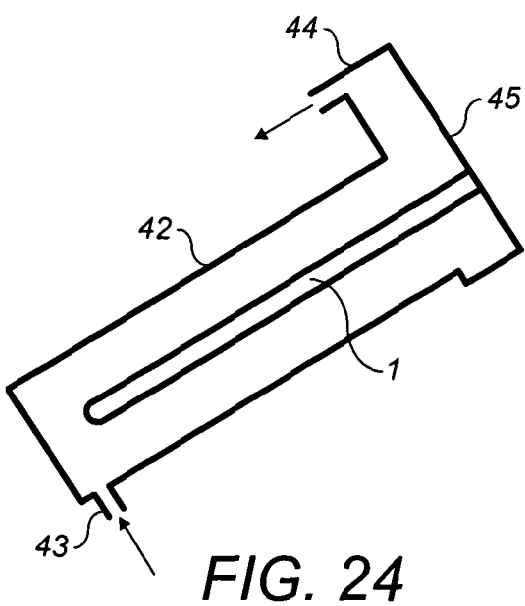
FIG. 24

WATER PURIFICATION APPARATUS COMPRISING AN UV SOURCE

CROSS-REFERENCE TO RELATED APPLICATION(S)

This application is a National Phase Patent Application and claims priority to and benefit of International Application Number PCT/GB2010/051795, filed on Oct. 26, 2010, which claims priority of GB Patent Application Number 0918824.4, filed on Oct. 27, 2009, and GB Patent Application Number 1003794.3, filed on Mar. 8, 2010.

This invention relates to purification. In particular it relates to water purifying apparatus.

Water cooling machines and other dispensing apparatus is generally required to dispense water which is purified and potable. Ultraviolet (UV) systems are often used to purify water. These work by irradiating the water with UV radiation which serves to destroy bacteria and other microorganisms.

Whilst water coolers and similar dispensing machines used in domestic, office or factory environments for example are very efficient at purifying water to a sufficient level to be drinkable and destroying microorganisms present in the water when received from a source, problems can sometimes arise with organisms at the actual dispensing point or faucet. Thus, water which has been treated and purified may pick up contamination at the point of dispense. A weakness of present UV systems is therefore post UV sterilisation, where water might be re-contaminated. Back contamination through machine nozzles is also a known issue, either by natural bacteria proliferation or human contamination, as is stagnation of water over relatively short periods, which facilitates organism growth in any storage media.

The present invention arose in an attempt to provide an improved purification apparatus, in particular an improved water dispensing apparatus.

According to the present invention in a first aspect there is provided a purification apparatus, comprising an elongate UV source and a conduit for water, or another fluid, to be purified, the conduit being formed of a UV transmissive material, wherein the conduit has an inlet and an outlet and is positioned so that part of it is wrapped around at least part of the UV source thereby to sterilise water or fluid within the conduit, further comprising reflective means for causing UV radiation to be reflected onto one or more parts of the conduit which extends beyond the part which is wrapped around the UV source.

With such an arrangement, by reflection, UV radiation on all parts of the conduit is enhanced.

According to the invention in a further aspect there is provided apparatus for a flowable substance comprising a vessel, formed of a UV transmissive material, for a flowable substance, means for receiving a UV source in such a disposition that a substance contained within the vessel is acted upon direction by UV radiation from the UV source, an inlet and an outlet to the vessel, further comprising reflective means for causing UV radiation from the lamp to be reflected onto at least part of the inlet and/or outlet.

The invention, in a further aspect, comprises a liquid holding device comprising means for receiving a UV source in such a disposition that liquid contained within the holding device is acted upon by UV radiation from the UV source, an inlet and an outlet to the liquid holding device, further comprising reflective means for causing UV radiation from the lamp to be reflected onto at least part of the inlet and/or outlet.

Preferably, the reflective means comprises a cap through which at least the outlet passes and which has a surface which reflects UV radiation, thereby reflecting some UV radiation from the source onto one or more parts of the vessel/conduit. A UV reflective chamber is preferably mounted over the part of the sleeve that is wrapped around the UV source and thereby reflects UV that has been transmitted through the conduit back through the conduit and to all parts of the chamber.

In a preferred embodiment, a faucet is provided, the faucet being made of a UV reflective material and positioned such that a portion of UV radiation is reflected by the faucet onto the outlet and/or inlet of the conduit, thereby to sterilise water at the outlet and/or inlet.

With conventional dispensers, microorganisms might enter at the point of dispense from the outlet or be present upon the faucet itself and these could contaminate the water which has previously been sterilised, as it passed a UV source. By the provision of a faucet and/or end cap which are positioned to reflect at least part of the radiation from the lamp to the end, or a part very near the end, of the water conduit, then these microorganisms can be treated. This can greatly improve the efficiency and effectiveness of sterilisation and lead to better quality drinking water. This also prevents back contamination whereby micro organisms and contamination can be introduced through the dispensing nozzle/faucet.

Preferably, the cap has a surface adapted to reflect UV radiation to a part of the conduit which is not wrapped around the UV source. The cap may have at least one internal surface arranged to reflect UV radiation onto at least part of the inlet and/or outlet of the conduit.

The reflective internal surface of the cap may be tapered towards the outlet of the conduit. The reflective internal surface of the cap may comprise a bottom surface, a top surface and side surface extending between the top and bottom surfaces, wherein at least the side and/or top surface is tapered towards the outlet.

Preferably, the reflective internal surface converges as it extends away from the UV source.

The cap may have an extent in one direction which is greater than its extent in the other direction. The cap may be generally segment shaped in a cross section. The cap may have a first curved end of a first radius of curvature and a second curved end of a second, larger, radius of curvature in cross section. These curved ends may be joined by straight sides. The UV source may extend axially within or partially within the second curved end and the outlet of the conduit may lie axially within the first curved end.

By virtue of such a tapered/converged/segment-shaped arrangement, as the distance from the UV source increases, the reflected radiation may be concentrated, preferably towards a point at which the outlet of the conduit is provided, so as to effectively irradiate the outlet of the conduit by the reflected radiation.

The reflective cap preferably provides a reflective path which extends beyond the outer radial extent of the conduit.

The faucet may be positioned such that it reflects UV radiation onto the outlet. The faucet may comprise part of the cap. In any case it is preferable that the faucet is connected to the cap to form an unbroken refractive path.

Preferably, the conduit extends into the faucet but stops short of the end of the faucet so that the outlet of the conduit is recessed with respect to an outlet of the faucet. The portion of the conduit extending into the faucet may be shielded by the faucet from direct radiation from the UV source.

The apparatus may include a chamber having an internal UV reflective surface which is mounted over the wrapped part of the conduit thereby to reflect radiation back to the conduit. The chamber may terminate in the cap.

The wrapping may be done by providing the vessel/conduit in the form of a coil or helix which is positioned around a UV source.

The UV source may be one or more UV lamps. It will most preferably be a UVC source.

The inlet and outlet of the conduit may be positioned at the same end of the apparatus or at opposite ends of the apparatus.

In accordance with the invention in a further aspect, there is provided an inline water purification apparatus, comprising a conduit for the water to be purified, the conduit being wrapped around an elongate UV source and having an outlet, and a reflective means positioned such that UV radiation is reflected by the reflective means onto the outlet.

A faucet may be provided which has a reflective surface and is positioned so as to reflect UV onto the outlet.

Embodiments of the invention can ensure that all water purifier types are purified at the point of dispense, while mitigating back contamination. The invention can be used with, inter alia, ambient, sparkling and cold water or other fluids.

Embodiments may also be used with many other types of liquid, fluid or other flowable substances.

Embodiments of the invention will now be described, by way of example only, with reference to the accompanying drawings in which.

Figure 3A:
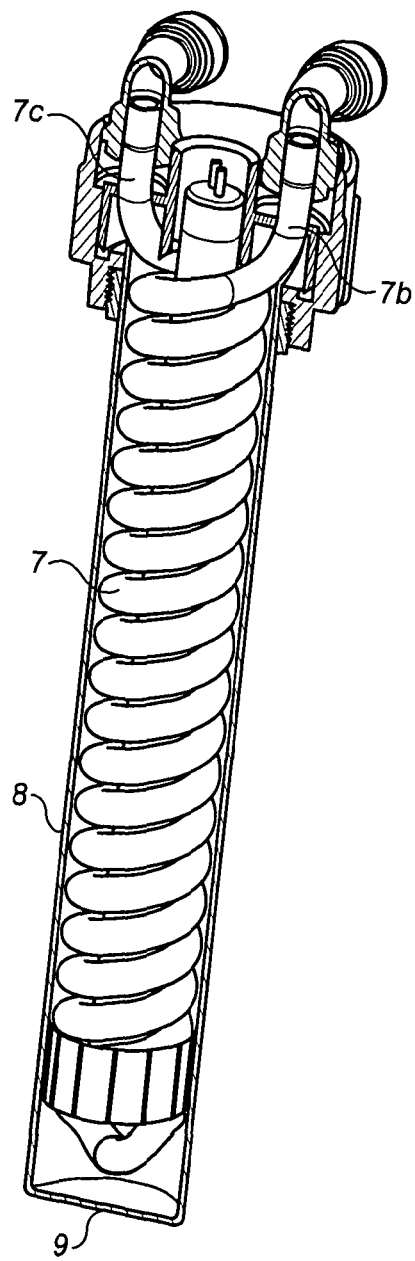
Figure 8A:
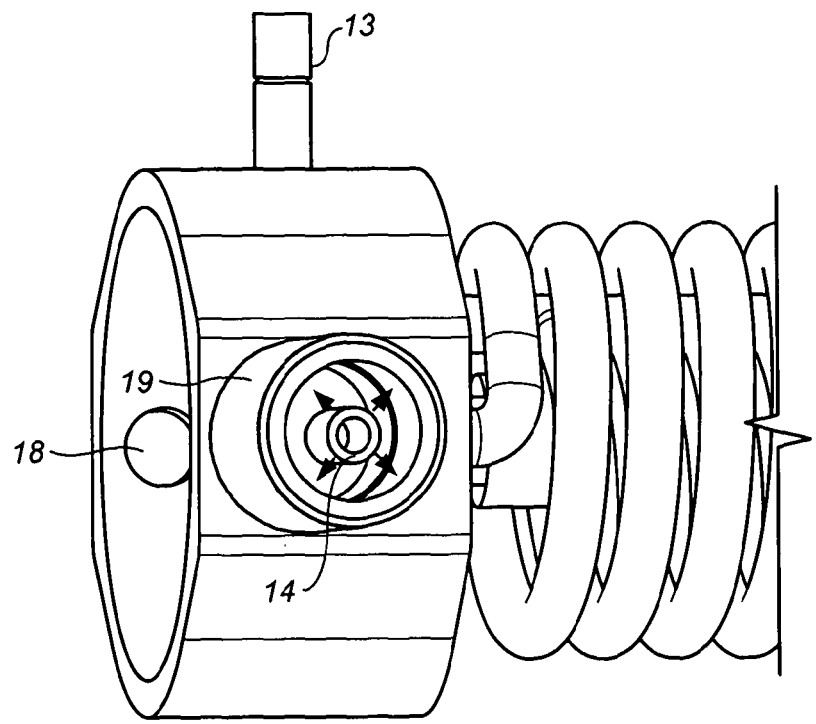
Figure 9:
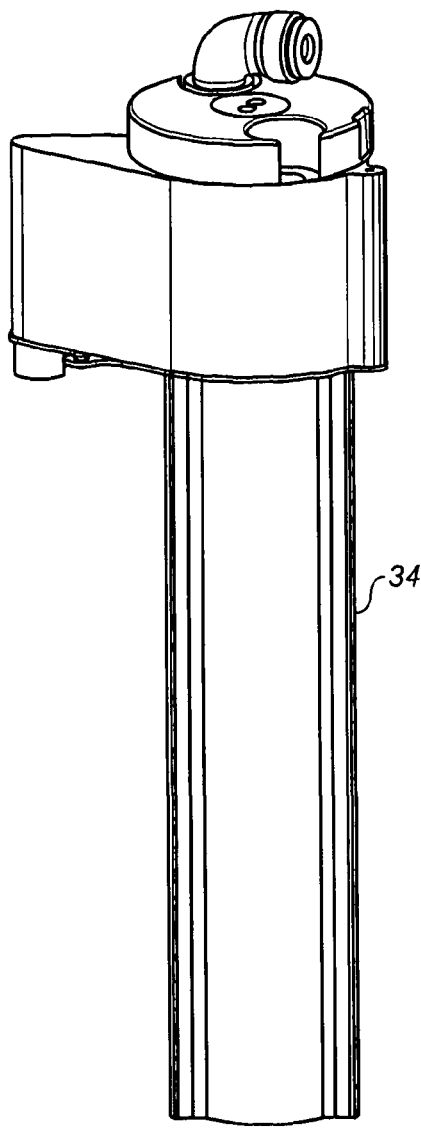
Figure 10:
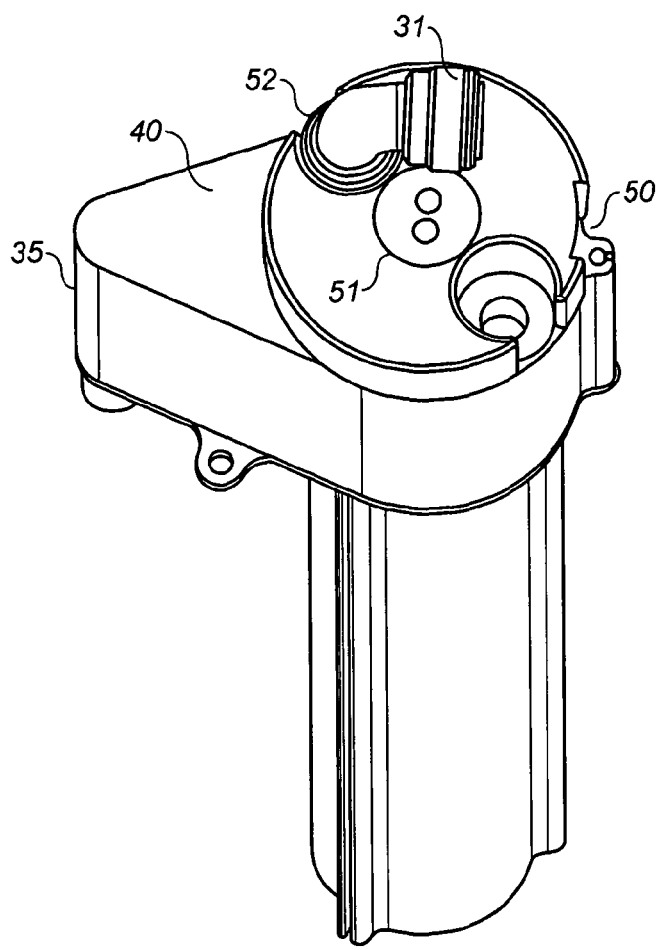
Figure 11:
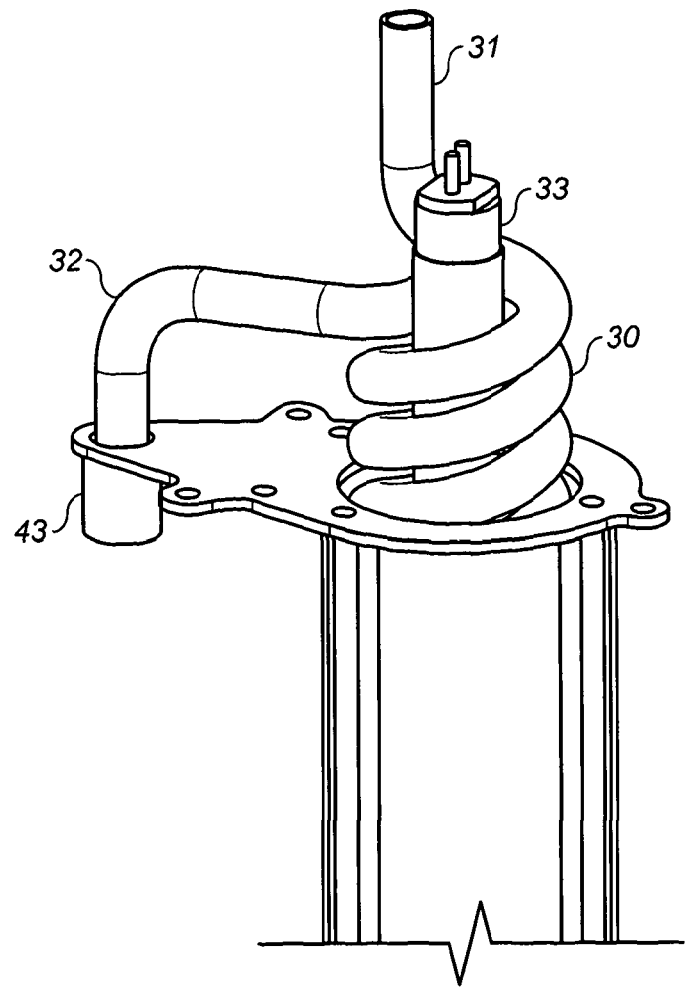
Figure 12A:
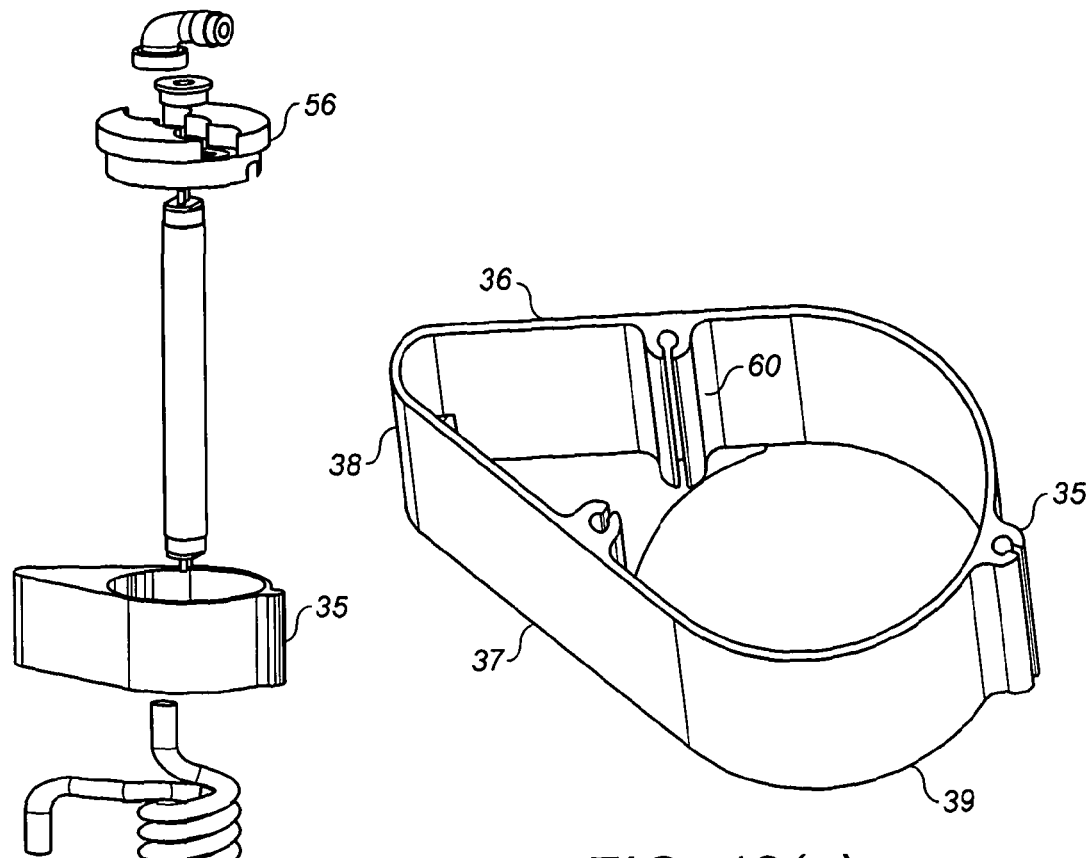
Figure 12:
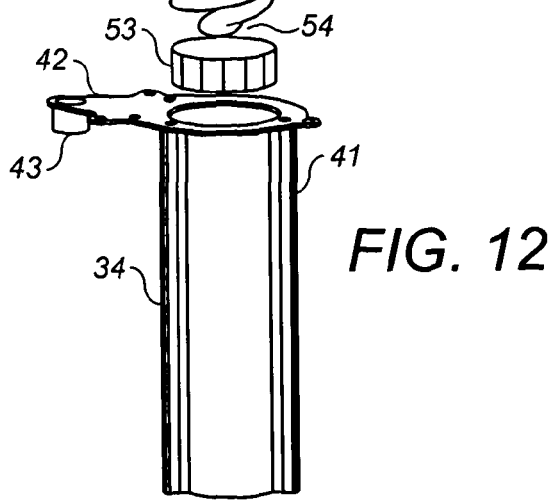
Figure 12B:
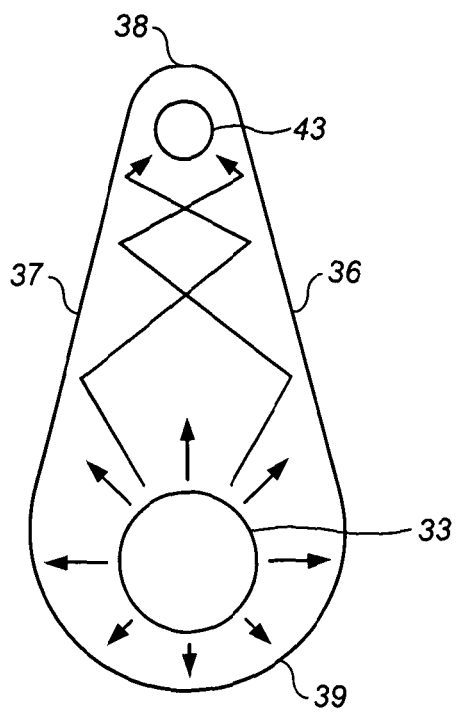
Figure 12C:
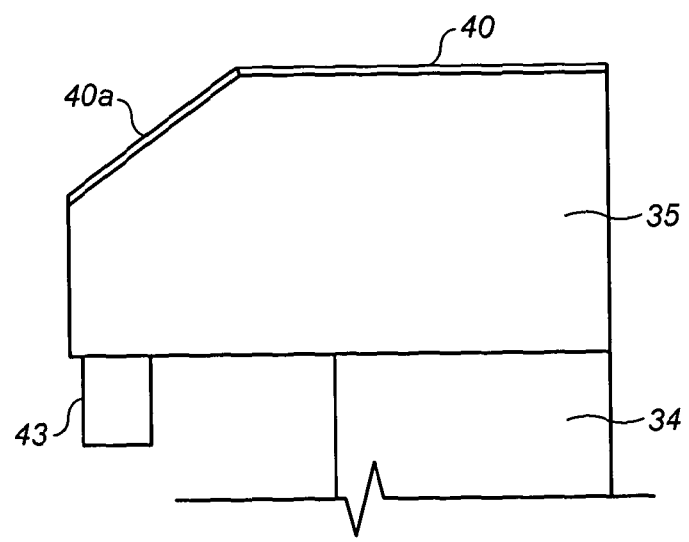
Figure 13:
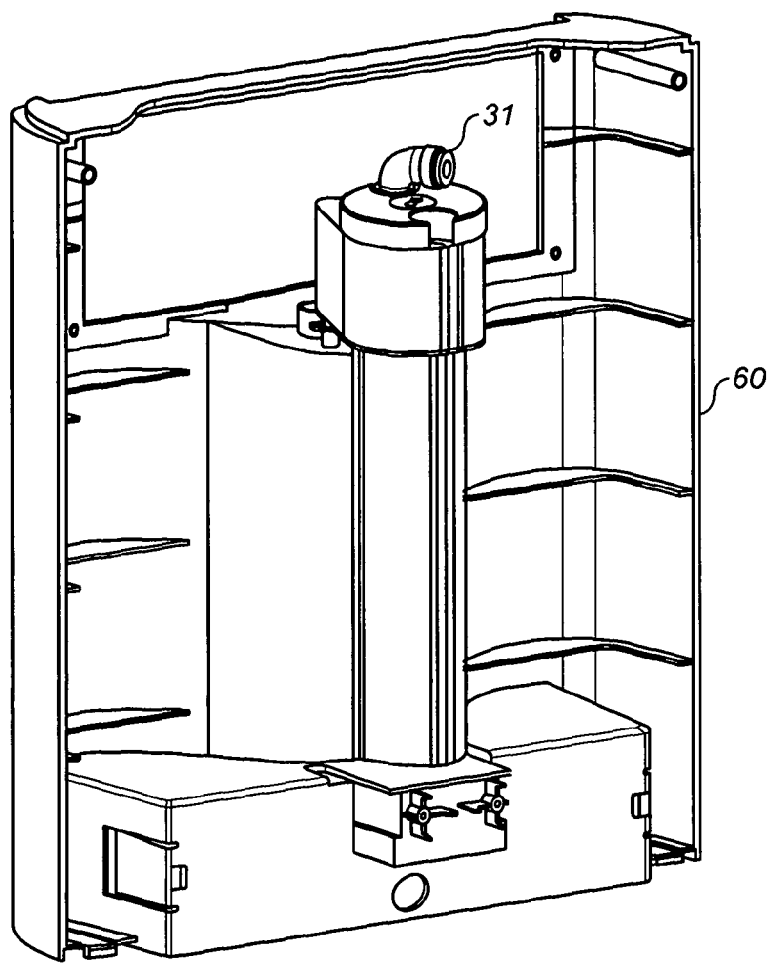
Figure 14:
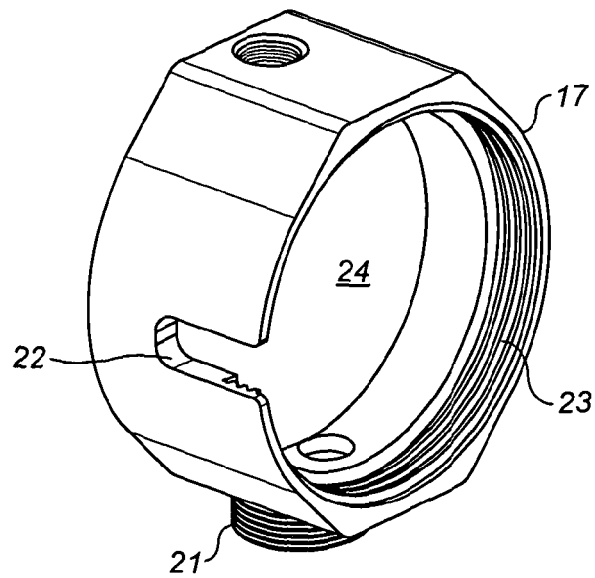

FIGS. 3(a) and (b) show a partial cross-sections through a sterilising apparatus;

FIG. 4 shows an alternative apparatus including a faucet;

FIG. 5 shows the apparatus of FIG. 4 with end cap removed;

FIG. 6 is an exploded view of some of the components of the embodiments of FIGS. 4 and 5;

FIG. 7 a view of an end of the second embodiment;

FIGS. 8(a) and (b) is a view from above of an end of the second embodiment with cap removed;

FIG. 9 shows a third embodiment;

FIG. 10 is an alternative view of the third embodiment;

FIG. 11 is a view of the third embodiment with part of the cap removed;

FIG. 12 is an exploded view of parts of the third embodiment;

FIG. 12(a) shows a perspective view of part of the cap;

FIG. 12(b) shows a partial sectional view of the cap, illustrating the concentration of the UV radiation;

FIG. 12(c) shows a side view of the third embodiment with a chamfered front;

FIG. 13 shows a sterilising unit of the third embodiment mounted in a water dispenser; and FIG. 14 shows an end cap.

Figure 15:
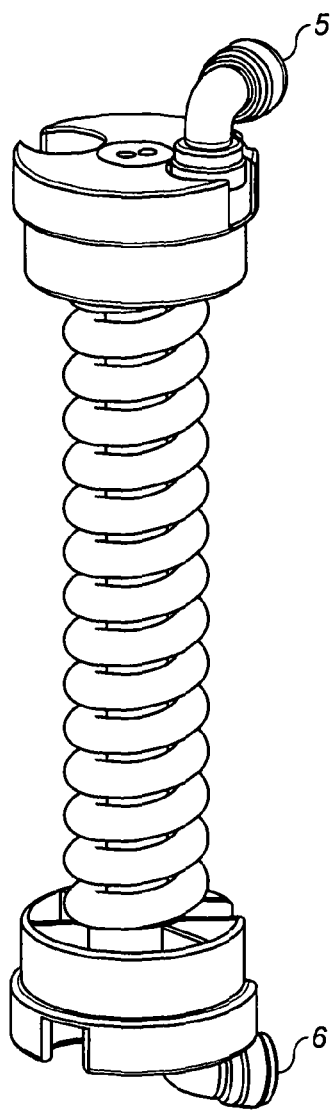
Figure 16:
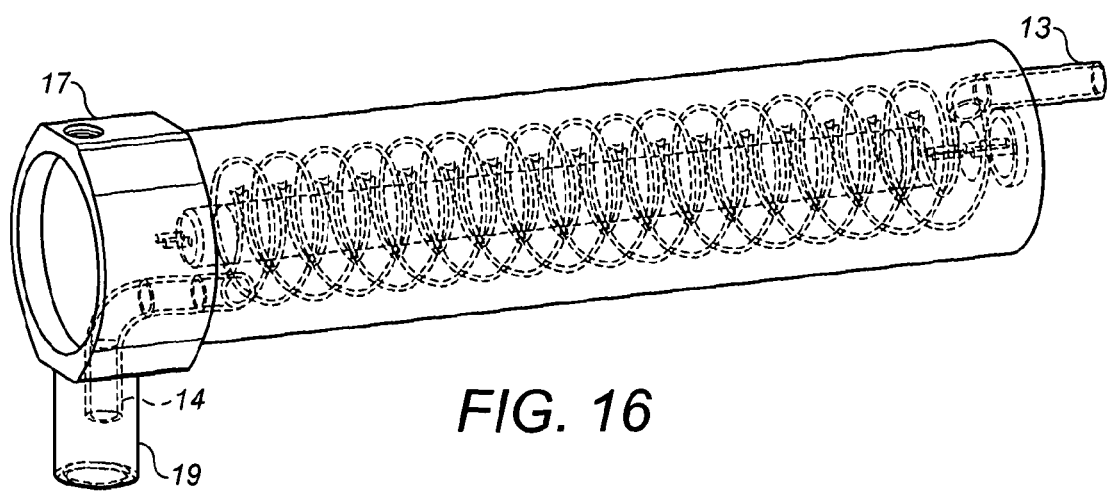
Figure 17:
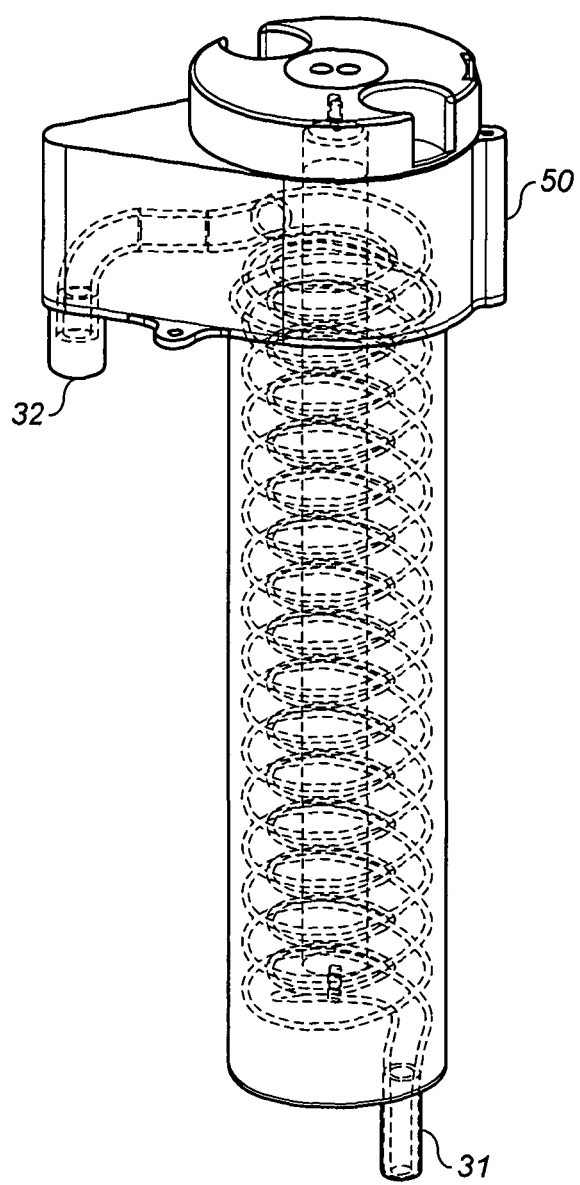
Figure 18:
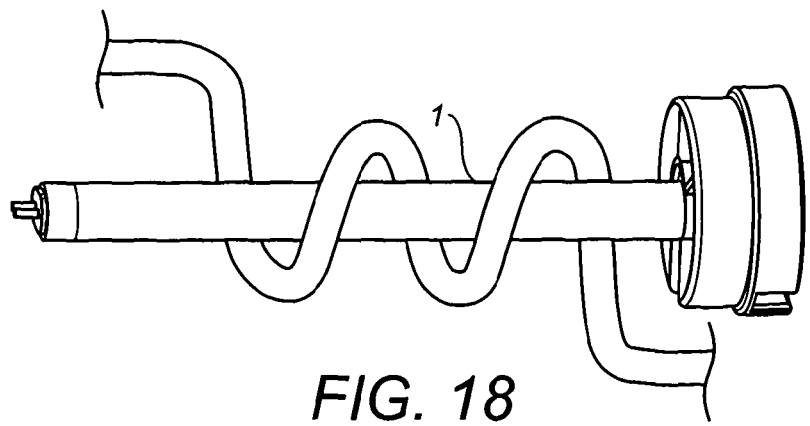
Figure 19:
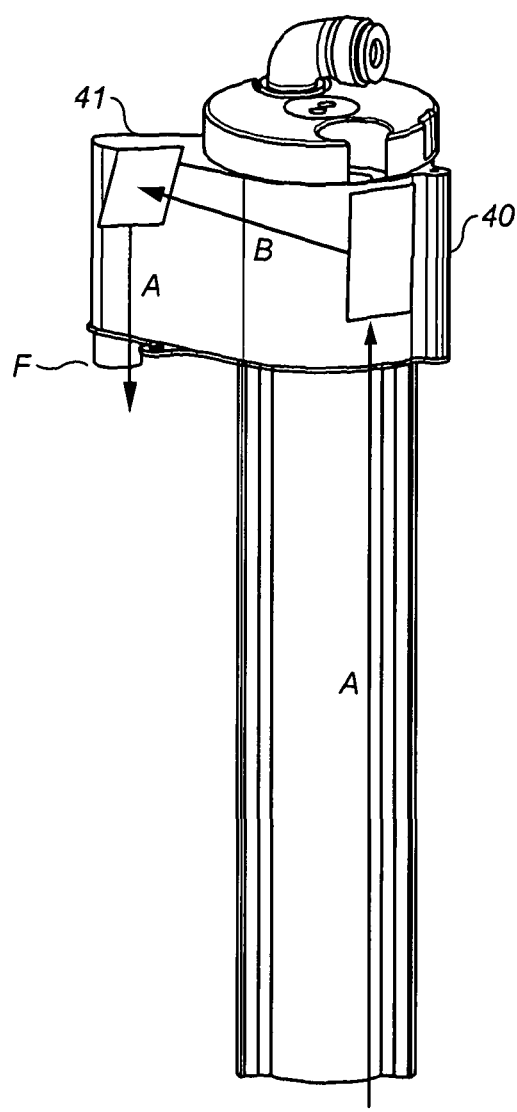
Figure 20:
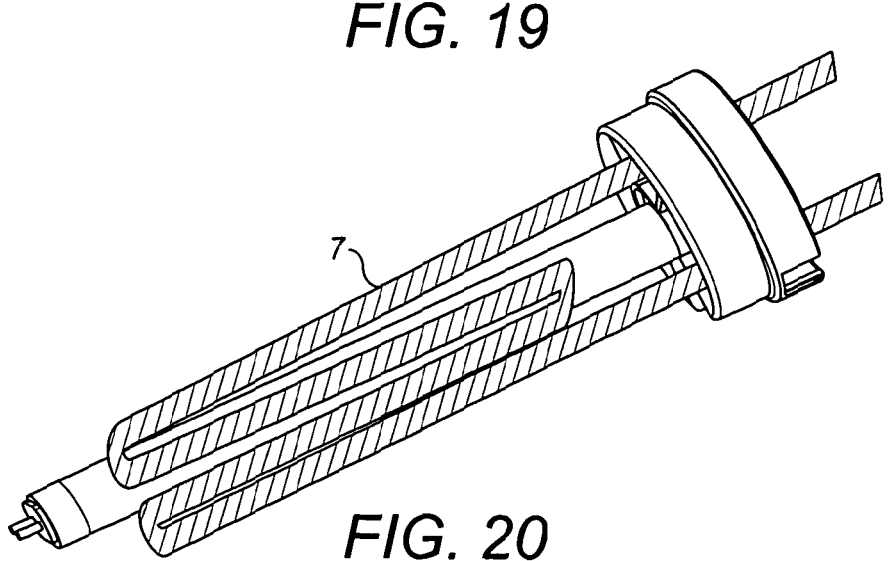

FIG. 15 shows a fourth embodiment with the water inlet and outlet at opposite ends;

FIG. 16 shows a fifth embodiment with the apparatus including a faucet;

FIG. 17 shows a sixth embodiment with a wedge-shaped reflective end cap;

FIG. 18 shows an embodiment having a lower number of turns;

FIG. 19 shows an embodiment using mirrors;

FIG. 20 shows an embodiment with an alternative conduit/sleeve;

FIG. 21 shows an alternative conduit design;

FIGS. 22 and 23 show alternative UV lamp designs; and

FIG. 24 shows a further embodiment.

Figure 1:
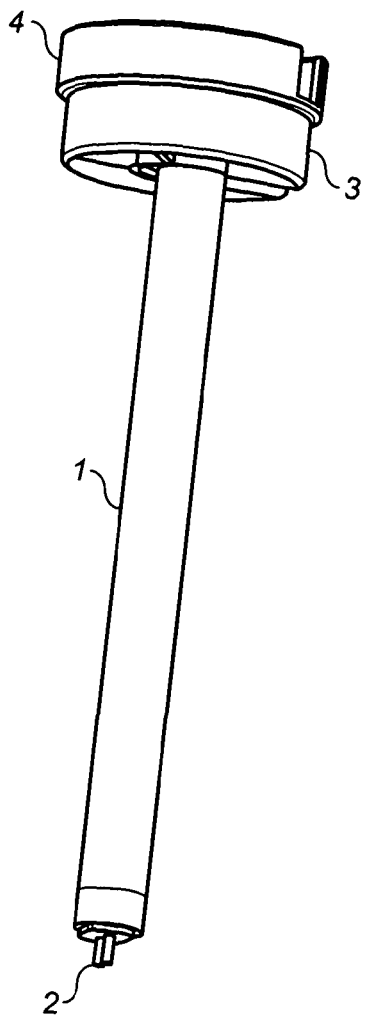
FIG. 1 shows part of a UV sterilising apparatus.

FIG. 1 shows part of the sterilising apparatus for a water dispenser (which may typically be of the type known more commonly as a water cooler typically used in an office or other environment). Such water dispensers require the water to be properly sterilised before they are dispensed. Ultra violet (UV) sterilisation is often used for this. UV can destroy bacteria and other microorganisms effectively if used at the correct frequencies and intensities. These are well-known in themselves and are not the subject of this patent specification. Note that whereas the fluid will usually be water, it may be other fluids or beverages.

FIG. 1 shows a typical UV source in the form of an elongate UV lamp 1. This has electrical connections 2 for connection to a power supply at one end and at the other end it is received in an end cap/cover 3 which has a cylindrical shroud portion 4 encircling an end portion of the UV lamp 1. The UV lamp 1 is arranged to generate UV radiation of a sufficient frequency and intensity to destroy a sufficient level of microorganisms so that water acted upon thereby is sterilised to certain standards, as will be known in the art.

Figure 2:
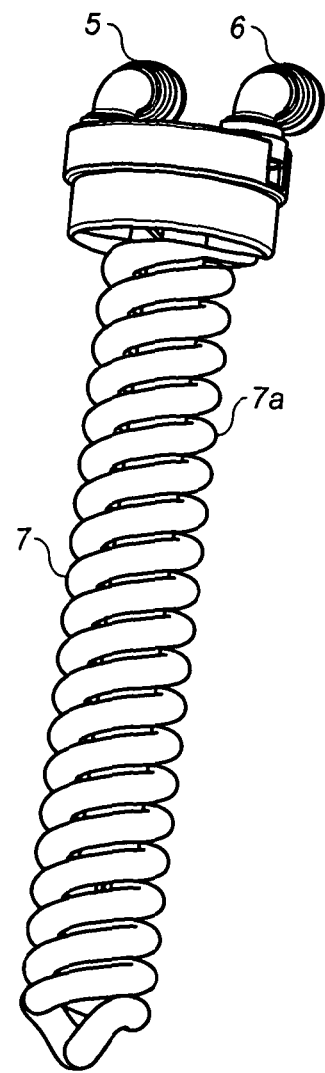
FIG. 2 shows the sterilising apparatus with a water conduit wrapped around.

FIG. 2 shows a conduit or tube in which the water is transported around the UV lamp. This shows a coiled (helical) conduit 7 connected at one end to a water inlet 5, positioned in use so that it is coiled around (possibly in contact with) the lamp 1 from the inlet end 5 to a bottom end and coiled up again to its other end where it connects to a water outlet 6. Thus, water to be sterilised passes through a coil which is tightly wound around the UV lamp in order to be sterilised thereby. The inlet and outlet are most preferably provided at the same end of the source as shown in FIG. 2.

Alternatively, the inlet 5 and outlet 6 can be provided at opposite ends as shown in FIG. 15.

FIG. 3 shows how an outer shroud or casing (outer chamber) 8, being generally cylindrically-shaped and having a closed end 9, is positioned, in use, over the top of the conduit 7 and secured to the end cap 3. This is formed of a UV reflective material, such as aluminium. Note that the sleeve or conduit 7 will be made of a UV transmissive material and a typical example which is preferably used is of quartz. The aluminium chamber is formed of any material that is reflective of UV. Although preferably of aluminium, it may be of other metals, plastics or other material which is reflective. This serves to reflect UV radiation which has passed through the sleeve, back through the sleeve and so enhances and improves the sterilisation of fluid within the parts of the sleeve which lie between the lamp 1 and chamber 8.

The cap 3 is also of reflective material and may also be made of aluminium, steel or any other reflective materials.

It seen, particularly from FIG. 3(a), that the extremities of the sleeve 7b 7c do not form part of the coiled portion 7a and they connect to the inlet 5 and outlet 6. However, since the cap is reflective, then this reflects some of the UV radiation from the UV source 1 to these extreme parts 7b, 7c of the sleeve and ensures that these extreme parts of the sleeve are still acted upon by UV radiation. Thus, any microorganism which may be present at the parts of the sleeve which are not directly in the coiled portion adjacent to the UV lamp, are still subject to UV sterilisation by virtue of the UV radiation being reflected from the end cap or chamber.

The end cap may be of any suitable design. It is preferably cylindrical as shown for maximum effect but may have a square or other internal shape. It may include baffles or other parts that impinge closer to the extreme end portions of the sleeve thereby to improve sterilising efficiency. The chamber 9 preferably connects directly to the end cap so as not to leave a gap or space which UV radiation may escape from.

Figure 3B:
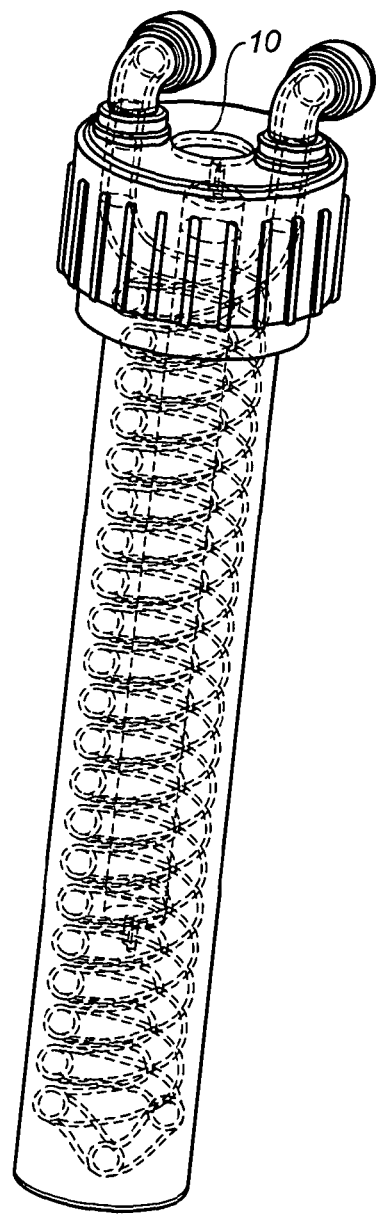

The end cap may preferably be closed-ended, including a closed end 10, as shown in FIG. 3b, which has openings, apertures or as otherwise shaped to receive the inlet and outlet connections 5 and 6. This closed end 10 or end wall also serves to reflect UV radiation back towards the sleeve 7.

FIGS. 4 to 8 show an alternative embodiment. This again comprises a UV lamp 11. This may be of 11 W for example, but other lamps may be used. A spiral quartz sleeve 12 having a spiral part similar to that of the first embodiment acts as the conduit for water to be sterilised and includes an inlet 13 and outlet 14 provided at the same end. Thus, water to be sterilised enters through inlet 13, moves in a spiral manner down towards lower end 15 of the sleeve and then back up to outlet 14, again in a spiral manner. The sleeve is positioned over the elongate lamp 11 in a similar way to that of the first embodiment so that it is in effect wrapped around the lamp and water passing through it is sterilised.

A UV-reflective chamber or case 16, which may be of aluminium, such as anodised aluminium, or any other UV reflective metal, plastics or other material is mounted over the sleeve 12 and again acts to reflect radiation back through the quartz sleeve. Note again that in any embodiment the sleeve may be of quartz or other material which is UV transmissive.

A silicone, rubber or other bung 17 covers the end of the UV lamp having connections to the power supply and control circuit.

A UV reflective cap is mounted at the end of the quartz sleeve bearing the inlet and outlet and the anodised aluminium case or other chamber 16 is connected to this. This is again typically of aluminium, such as anodised aluminium, or other materials having the desired reflective properties. It includes recesses, orifices or other parts or shaping to accommodate the inlets and outlets of the quartz sleeve and also, in this embodiment, means for receiving a conduit for a hot water supply 18.

In the preferred embodiment, the water acted upon the sterilising unit may be cold (ie chilled) or ambient temperature water and may be still or sparkling.

In this, and some other embodiments, a faucet 19 is provided. This receives the outlet 14 from the quartz sleeve which extends a certain extent into the faucet. The faucet 18 is again of UV reflective material and will typically be of stainless steel although again it may be of any metal or plastics material that is reflective.

The outlet 14 from the sleeve includes a bend 14a, typically a right angle or approximately a right angle and the end part of this extends into the faucet.

Because the faucet 19 is reflective this also, in combination with the end cap 17, causes some of the UV radiation from the lamp to be reflected directly to the outlet 14 and thus any bacteria or other microorganisms which might be present at the faucet can also be sterilised.

The reflective end cap 17 maximises UV strength as UV light is reflected inside of the chamber 16.

The chamber, as described, causes UV to be directed to the end portions of the sleeve. It includes an end wall 24 which may be spaced a distance from the end of the side walls 21 and the means for receiving a conduit for a hot water supply 18 is typically positioned on this end wall, as shown in FIG. 4. The hot water pipe also extends a length into the faucet 19. Thus, in this embodiment, the hot water system is kept separate although a degree of sterilisation of the hot water may still occur at the faucet.

Figure 8B:
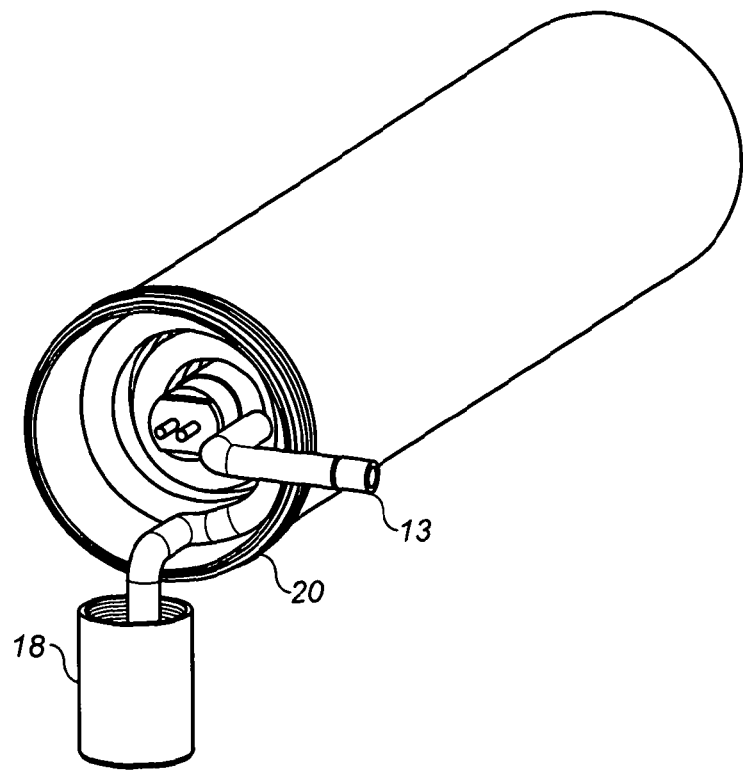

FIGS. 8(a) and 8(b) show the cold/ambient outlet 14 extending into the faucet. The figures show how UV is exposed to the faucet where it is reflected back to the coil stream, thus having UV sterilising properties which can be used to affect microorganisms at the outlet if there are any. FIG. 8(b) shows that the aluminium chamber or case 16 may have an end which has a screw-thread or other means for connecting to a cooperating screw-thread (shown in FIG. 14) on the aluminium cap 17. It may be connected in other ways but it will be preferable to have a reliable unbroken connection between the case and cap for best UV efficiency. The screw-thread is designated by 20 in FIG. 8(b).

FIG. 15 shows a fifth embodiment of the invention. This is very similar to the invention illustrated in claims 4 to 8 but with the inlet 13 and outlet 14 on different ends of coil 12.

FIG. 14 shows a typical end cap 17. This may include an inlet, aperture or hollow boss 21 which receives the inlet 13 of the quartz sleeve, and a cut-out 22 which receives the outlet 14 of the sleeve. This also shows the screw-threaded portion 23 which cooperates with the screw-threaded end 20 of the chamber and the end face 24. As described, it may have other configurations.

FIG. 7 shows how UV radiation is emitted towards the end cap 17, from where it is reflected.

FIGS. 9 to 12 show a further embodiment. This embodiment functions similarly to that of the second embodiment above. A spiral (helical) core sleeve 30 is again provided having inlets and outlets 31, 32 at the same end as before. This is mounted over a UV lamp, an end of which 33 is shown in FIG. 11, and an outer chamber or cover 34 of anodised aluminium or other reflective material is placed over this. The outer chamber is most preferably stainless steel of a grade that offers suitable reflectivity. The inner surface may be polished to maximise reflectivity.

A reflective end cap 35 is also provided, but in this embodiment the end cap has a cross-section which is generally segment-shaped but has curved ends, as shown most clearly in FIGS. 10, 12(a) and 12(b). As shown, this end cap 35 has two straight walls 36, 37 converging to a first curved end 38 having a relatively small radius of curvature and, at the other end, being joined by a further curved end 39 having a larger radius of curvature, thus forming a curved segment or wedge shape as shown most clearly in FIG. 12(a). Straight walls 36, 37 and curved ends 38 and 39 together form a side surface, which extends between a top surface, formed by an end plate or cover 40, and a bottom surface, formed by a projection or extension 42 (described below). These surfaces may be considered, in combination, to comprise a reflective internal surface of the cap 35, which surface, as clearly shown in the figures, tapers towards the outlet of the conduit. Put differently the internal surface converges as it extends away from the UV source. This provides the benefit that reflected radiation is concentrated towards the faucet 43 and the outlet of the conduit situated therein. Such concentration of reflected radiation is illustrated in FIG. 12(b), which represents a partial sectional view of the end cap 35.

Mounting means or detents 60 are provided for mounting the chamber 34 to the end cap 35, however, in alternative embodiments these may be omitted or provided externally, so as to provide a smooth reflective internal surface.

End plate or cover 40 covers the end of the end cap remote from the chamber/sleeve end. This end cap will also be of UV reflective material, typically the same material as the cap which may be aluminium or any other metal or plastics material that has suitable reflective properties. The end plate or cover 40 may also be tapered towards the outlet of the conduit, as shown in FIG. 12(c) at 40a in which case the sidewalls 36, 37 and curved end 38 are chamfered to accommodate the tapered cover 40. This further aids in reflection of the IR radiation towards the faucet.

Although a specific shape is shown, any suitable shape, cylindrical or non-cylindrical, or other shape, including such as elongate shapes, may be used. The purpose of this will be described below.

Note that the chamber 34 in this case comprises a generally cylindrical portion 41 as before, but also includes, at its open end, a transversely extending part such as a projection or extension 42 leading to a cylindrical part (faucet) 43 that in use, as shown in FIG. 11, receives the outlet 32 from the water sleeve 30 and is of diameter large enough to accommodate the outlet 13. This will preferably all be formed as one integral chamber unit, although these parts may be separate, but the cylindrical part 41 and at least the second cylindrical projection 43, receiving the outlet from the sleeve, should be of UV reflective materials. This extension hollow cylindrical part 43 acts as a faucet. The portion of the conduit within the faucet 43 is shielded by the faucet from direct radiation. The outlet of the conduit is recessed from the end of the faucet to prevent contamination. In alternative arrangements, a separate faucet may be attached to it, which is also reflective.

A rubber bung 56 is mounted on the cap and this is generally circular in this embodiment, having its radius matching the curved part 39 of the end cap and this includes orifices 51 for connecting to the end 33 of the lamp electrically. This also includes an orifice 52 for the inlet 31 of the core sleeve.

A spacer 53 may be provided to space the bottom end 54 of the sleeve from the closed end 55 of the chamber. This may be of rubber, for example.

Thus, in this embodiment UV is again reflected from the end cap to act upon microorganisms present at the outlet (and also the inlet) of the sleeve and the faucet is of reflective material and forming an unbroken reflective surface with the end cap, aiding in the sterilisation.

FIG. 16 shows a sterilising apparatus as in the third embodiment mounted to the inside of a water dispensing machine 60. Water enters through inlet 31, is sterilised and then is dispensed through the faucet to the outside of the machine.

FIG. 17 illustrates a further embodiment. This sixth embodiment is very similar to the third embodiment described above but with the inlet 31 and outlet 32 provided at opposite ends of the apparatus.

A UV light sensor or UV monitor may be used to control UV radiation.

Note that any different shape/configuration of component, lamp, conduit, others can be used with any embodiment of the invention.

FIG. 18 shows an embodiment in which the conduit 7 has inlets and outlets but is only wrapped a few times around the UV lamp 1. In embodiments in which a conduit is provided which wrapped around the lamp, there may be any number of turns from one upwards. In the example shown in FIG. 18, the inlet and outlet are at a respective opposite ends of the apparatus, although it will be clear that these may be provided at the same end of the apparatus.

FIG. 19 shows an embodiment in which specific mirrors 40, 41 are provided. In the embodiment shown in FIG. 19, these are provided at the end cap and positioned in a 'periscope' type arrangement so as to reflect UV radiation from a first direction A through 90° and then through 90° in a direction B, through a further 90° to a direction—A direct to the faucet area F. Of course, just one mirror could be provided or two or more and they can be arranged to reflect radiation at any particular angle or combination of angles. These may be provided with embodiments other than with a reflective end cap and may, in some embodiments, form part of the reflective arrangement having other reflective parts of be the sole reflective arrangement. The mirror should, of course, be made of the material or have a surface that reflects UV radiation.

FIG. 20 shows an arrangement in which the tube or conduit 7 is wrapped not a helix but in a series of lines in a generally longitudinal direction relative to the axis of the UV lamp. In their entirety, the parallel lines (which need not be exactly parallel to each other) are still in effect wrapped around the lamp albeit longitudinally rather than transversely. This can again be used with any embodiment. In some other embodiments, the conduit may have a combination of one or more turns and one or more longitudinally arranged portions.

One further embodiment, comprises a helical arrangement which extends from an inlet at one end to a number of helical turns down to the remote end then a single return line which is not wrapped around the UV source back to an outlet at generally the same end as the inlet. Although most embodiments described above include a single lamp, there may be more than one lamp. For example, there could be two lamps in series or in parallel and the lamps could be provided either longitudinally spaced (as shown very schematically in FIG. 22), parallel or perhaps with an angle between them such as 90° or another angle. FIG. 23 shows two lamps in parallel schematically. In addition to being in parallel, two or more lamps may be provided which are themselves coiled together in some embodiments.

Many other configurations and dispositions and numbers of lamps will be apparent.

The above embodiments include a vessel in the form of conduit (eg tube or pipe). In other embodiments the water may be provided simply to a tank which envelopes or partially surrounds the UV source or sources. This is conceptually shown in FIG. 24. The UV lamp 1 is provided inside a water tank 42, water enters through an inlet 43 and out through an outlet 44 and again a reflective end cap or other reflective means 45 is provided for reflecting some UV radiation to the outlet.

Thus, the invention is applicable not only to embodiments where water (or any other fluid or flowable substance) is retained within a conduit or tube, but to any where it is held within a vessel, including tanks, reservoirs, tubes, conduits or other apparatus that can hold such substances.

The invention is also applicable to many other fields, for other fluids or flowable substances, including many different beverages, pharmaceutical applications (for sterilising substances or in the manufacture of pharmaceuticals), other industries where sterilisation of flowable substances is necessary, aquarium or pool cleaning or other applications, showers (where pure water can be dispensed), care homes, hospitals, catering establishments, laboratories and other environments, the electronics industry, eg for treating solder or other materials, and so on.

Apparatus embodying the invention may be incorporated in apparatus, such as water coolers, where the water has already been subject to initial filtering or sterilisation, perhaps by another UV system. In such systems, it may be incorporated at the outlet/dispensing end for example.

Many different types of vessels may be used, such as the conduits (tubes) discussed, tanks or other types of vessels.

The invention claimed is:

1. A purification apparatus, comprising an elongate UV source and a conduit for water, or another fluid, to be purified, the conduit being formed of a UV transmissive material, wherein the conduit has an inlet and an outlet through which the purified fluid is dispensed, and is positioned so that part of it is wrapped around at least part of the UV source thereby to sterilise water or fluid within the conduit, further comprising reflective means for causing UV radiation to be reflected onto one or more parts of the conduit which extends beyond the part which is wrapped around the UV source, wherein the reflective means comprises a cap having a generally wedge shaped internal surface adapted to reflect UV radiation to an outermost end of the outlet which is not wrapped around the UV source and which is spaced a distance radially outward from the wrapped portion of the conduit, wherein the substantially wedge shaped reflective internal surface of the cap is tapered towards the outlet of the conduit.

2. Apparatus as claimed in claim 1, wherein the cap has at least one internal surface arranged to reflect UV radiation onto at least part of the inlet of the conduit.

3. Apparatus as claimed in claim 1, wherein the reflective internal surface converges as it extends away from the UV source.

4. Apparatus as claimed in claim 1, wherein the reflective internal surface is arranged to concentrate radiation as it extends away from the UV source.

5. Apparatus as claimed in claim 1, wherein the cap has an extent in one direction which is greater than its extent in the other direction.

6. A purification apparatus comprising an elongate UV source and a conduit for water or another fluid to be purified, the conduit being formed of a UV transmissive material, wherein the conduit has an inlet and an outlet and is positioned so that part of it is wrapped around at least part of the UV source thereby to sterilise water or fluid within the conduit, further comprising reflective means for causing UV radiation to be reflected onto an outermost end of the conduit which extends a distance radially outwardly beyond the part which is wrapped around the UV source, wherein the reflective means comprises a cap having an internal reflective surface adapted to reflect UV radiation to the outermost end of the conduit, wherein the internal reflective surface of the cap is substantially wedge shaped.

7. Apparatus as claimed in claim 1, wherein the reflective internal surface of the cap comprises a bottom surface, a top surface and side surface extending between the top and bottom surfaces, wherein at least the top and/or side surface is tapered towards the outlet.

8. Apparatus as claimed in claim 1, wherein the reflective cap provides a reflective path which extends beyond the outer radial extent of the conduit.

9. Apparatus as claimed in claim 1, wherein a faucet is provided having a reflective surface and positioned such that it reflects UV radiation onto the outlet.

10. Apparatus as claimed in claim 9, wherein the faucet comprises part of the cap.

11. Apparatus as claimed in claim 9, wherein the faucet is connected to the cap to form an unbroken refractive path.

12. Apparatus as claimed in claim 9, wherein the conduit extends into the faucet but stops short of the end of the faucet so that the outlet of the conduit is recessed with respect to an outlet of the faucet.

13. Apparatus as claimed in claim 12, wherein the portion of the conduit extending into the faucet is shielded by the faucet from direct radiation from the UV source.

14. Apparatus as claimed in claim 1, including a chamber having an internal UV reflective surface which is mounted over the wrapped part of the conduit thereby to reflect radiation back to the conduit.

15. Apparatus as claimed in claim 14, wherein the chamber terminates in a cap.

16. Apparatus as claimed in claim 1, wherein the conduit is formed of quartz.

17. Apparatus as claimed in claim 1, including one or more mirrors forming at least part of the reflective surface.

18. Apparatus as claimed in claim 1, wherein the inlet and outlet of the conduit are provided at generally the same end of the apparatus.

19. Apparatus as claimed in claim 1, wherein the inlet and outlet of the conduit are provided at generally opposite ends of the apparatus.

20. Apparatus as claimed in claim 1, wherein the conduit includes one or more folded parts positioned generally longitudinally in relation to the UV source.

21. Apparatus as claimed in claim 1, wherein the conduit is a tank adapted to surround at least part of the UV source radially.

22. Apparatus as claimed in claim 1, wherein the UV source comprises two or more UV sources.

23. Apparatus as claimed in claim 1, including a vessel for a second source of flowable substance so as to enable a different source of substance to be dispensed directly without being directly impinged upon by radiation from the UV source.

24. Apparatus as claimed in claim 23, wherein the conduit for the second source of substance is positioned so as to receive at least some reflected radiation.

25. Apparatus as claimed in claim 1, wherein the cap has a first curved end of a first radius of curvature and a second curved end of a second, larger, radius of curvature in cross section.

\* \* \* \* \*